United States Patent [19]
Subramaniam

[11] Patent Number: 5,861,032
[45] Date of Patent: *Jan. 19, 1999

[54] MEDICAL DEVICE HAVING A BIOCOMPATIBLE COATING AND OXIDATION METHOD OF COUPLING THEREFOR

[75] Inventor: Raj Subramaniam, Fremont, Calif.

[73] Assignee: Surface Genesis, Inc., Sunnyvale, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 594,872

[22] Filed: Jan. 31, 1996

[51] Int. Cl.⁶ .............................. A61F 2/02; A61F 2/06; A61F 2/12

[52] U.S. Cl. ........................................ 623/11; 623/1; 623/8

[58] Field of Search ..................................... 623/1, 16, 66

[56] References Cited

U.S. PATENT DOCUMENTS

| | | | |
|---|---|---|---|
| 3,549,409 | 12/1970 | Dyck | 117/47 |
| 3,639,141 | 2/1972 | Dyck | 117/47 A |
| 5,045,318 | 9/1991 | Tengvall et al. | 424/422 |
| 5,152,993 | 10/1992 | Bjursten et al. | 424/422 |
| 5,308,641 | 5/1994 | Cahalan et al. | 427/2 |
| 5,336,518 | 8/1994 | Narayanan et al. | 623/1 |
| 5,354,736 | 10/1994 | Bhatnagar | 514/14 |
| 5,607,474 | 3/1997 | Cahalan et al. | |

OTHER PUBLICATIONS

Radionics, Inc., Neurosurgical Instruments, catalog sheet for Trigeminal Neuralgia Kit, 1981.

Primary Examiner—Mickey Yu
Assistant Examiner—John M. Black
Attorney, Agent, or Firm—Flehr Hohbach Test Albritton & Herbert

[57] ABSTRACT

A medical device for implantation in the tissue of a human body having a biocompatible coating thereon including a foreign body formed of a material which is substantially biocompatible with the tissue of the human body. The foreign body has a surface adapted to come in contact with the tissue of the human body and is capable of being oxidized. An organic linker is carried on the surface and forms an oxidative coupling with the surface. A bioactive agent is bonded to the organic linker by a chemical reaction or photochemical function.

12 Claims, 2 Drawing Sheets

MEDICAL DEVICE HAVING A BIOCOMPATIBLE COATING AND OXIDATION METHOD OF COUPLING THEREFOR

This invention relates to a medical device having a biocompatible coating and oxidation method of coupling therefor and particularly for medical devices made of metal and plastic.

Heretofore it has been found difficult to bind a bioactive molecule such as a peptide or a protein directly to the metal forming the medical device. One approach is to use a coating or a primer which when activated facilitates attachment of the bioactive molecule. Such primers have typically been in the form of polyurethane coatings or poly lactic acid or polyimide coatings. Such approaches have not been particularly satisfactory for several reasons. Bonding between the metal and the primer is not very strong and therefore there is a tendency for the bioactive agent to flake off. The primer itself is formed of a material which may be less biocompatible than the metal device which has been implanted. There is therefore need for a medical device having a biocompatible coating which overcomes these problems and a method for accomplishing the same.

In general, it is an object of the present invention to provide a medical device having a biocompatible coating thereon and an oxidation method of coupling therefor.

Another object of the invention is to provide a medical device and method of the above character in which the linker or base for the biocompatible coating is biocompatible.

Another object of the invention is to provide a device and method of the above character which utilizes the oxidation characteristics of the metal used in the medical device to covalently attach an organic linker to form an organic coupler.

Another object of the invention is to provide a device and method of the above character in which the organic coupler is utilized for attaching the bioactive molecule in the form of a peptide or a protein.

Another object of the invention is to provide a device and method of the above character in which the biocompatible coating can be rapidly and inexpensively applied.

Another object of the invention is to provide a medical device and method of the above character including implants formed of metal and of plastic.

Additional objects and features of the invention will appear from the following description in which the preferred embodiments are set forth in detail in connection with the accompanying drawings.

In general, the medical device is for implantation in tissue of the human body and has a biocompatible coating thereon comprised of a foreign body formed of a material which is substantially biocompatible with the tissue of the human body. The foreign body has a surface adapted to come into contact with the tissue of the human body. The surface of the foreign body is capable of being oxidized. An organic coupling agent is carried on the surface and forms an oxidative coupling with the surface. The coupling agent also carries a reactive group. A bioactive agent is bonded to the organic coupling agent by a chemical reaction.

In general, the method is for coupling a bioactive agent to a medical device implantable as a foreign body in the tissue of the human body. The medical device is formed of a material which is substantially biocompatible with the tissue of the human body and has an oxidizable surface coming into contact with the tissue of the human body. The method comprises the steps of removing any oxide present on the surface of the foreign body. Air or oxygen is then prevented from coming into contact with the surface of the body. An organic coupling agent is placed in contact with the surface to form an oxidative coupling with the surface of the foreign body. A bioactive agent is attached to the surface of the foreign body by reaction with the organic coupling agent.

Figure 1:
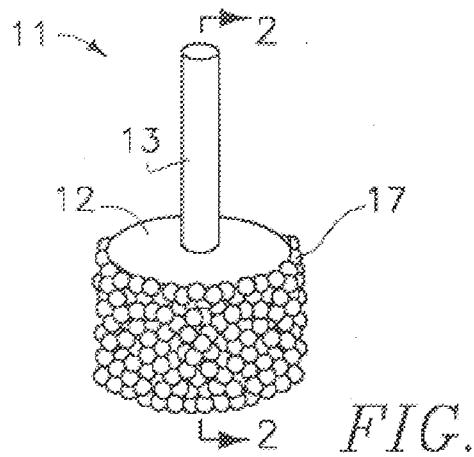
FIG. 1 is an isometric view of a dental post in which the base carries sintered titanium globules.
Figure 2:
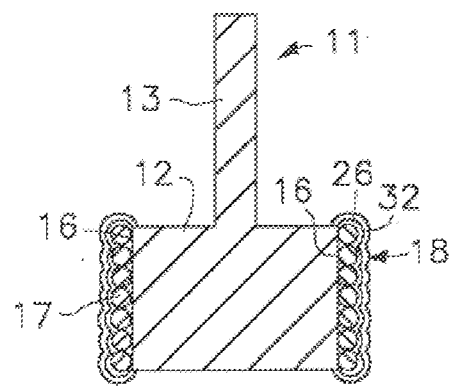
FIG. 2 is a cross-sectional view taken along the line 2—2 of FIG. 1 showing the dental post after it has been treated in accordance with the present invention to provide a biocompatible coating on the sintered titanium globules.
Figure 5:
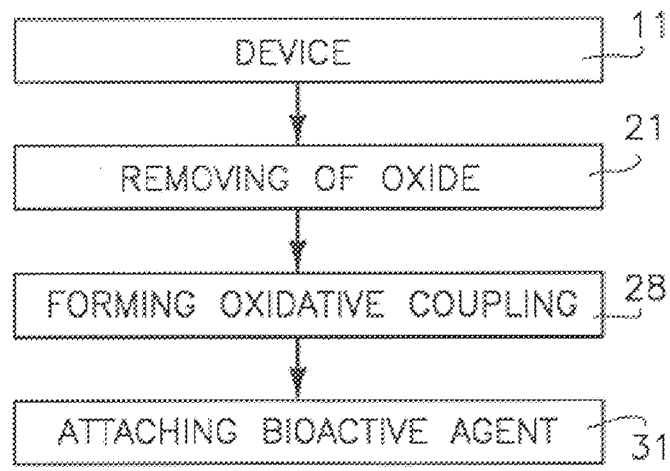
FIG. 5 is a flow chart showing the principal steps in the method of the present invention for coating metals.

More in particular, an example of a medical device incorporating the present invention as shown in FIGS. 1 and 2 and as shown therein is in the form of a dental post 11 which is provided with a cylindrical base 12 and a centrally disposed upstanding post 13. The dental post 11 is formed of a suitable biocompatible material such as titanium. The base 12 can have a suitable size as for example a diameter of 1 to 2 millimeters and a height of 2 to 3 millimeters whereas the post 13 can have a diameter ranging from 0.5 to 1 millimeter and a height ranging from 5 to 10 millimeters. The dental post thus far described is conventional and is utilized for implantation in the human jaw. Typically, the tooth is drilled to receive the cylindrical base 12 with the dental post 11 being utilized for supporting a false tooth which has been removed from the patient's mouth. In accordance with the present invention, it is desirable to coat the cylindrical base 12 with a biocompatible coating so as to promote bone tissue growth onto the cylindrical base 12 to thereby firmly secure the cylindrical base within the jaw of the patient. The cylindrical base 12 is provided with a cylindrical surface 16 which has sintered titanium microspheres or globules adhered to the surface in a conventional commercial process. The microspheres can have a suitable diameter as for example ½ of a millimeter and less. Described in another way, they can have a size of approximately one half the size of a conventional pin head. These microspheres 17 have been coated with a biocompatible coating in accordance with the present invention as described in connection with the step or flow diagram as shown in FIG. 5.

The medical device 11 can be considered as being a foreign body which is to be implanted into the tissue of the human body. This foreign body has a surface which is adapted to come in contact with the tissue of the human body. The material which forms the foreign body is one which has been selected in accordance with the present invention which is capable of being oxidized. They are made of suitable materials such as metal and plastic. Metals of particular interest are stainless steel, titanium and titanium alloys and particularly nickel titanium alloys. These materials have been selected because they are biocompatible with the tissue of the human body. The devices have surfaces which are adopted to come in contact with the tissue of the human body and with which it is desired to promote tissue growth. The surfaces of such materials are also characterized as being capable of being oxidized.

In accordance with the present invention, the medical device 11 which is to be treated in accordance with the present invention has any existing oxide thereon removed as shown by step 21. This oxide removal can be accomplished in a conventional manner such as by removing the same in an etching solution. One etching solution found particularly suitable for etching of titanium and titanium alloys is a mixture of 4% hydrofluoric acid, 30% nitric acid and 15% sulfuric acid with the balance being water.

The medical devices are placed in the etching solution for a period of 1 to 5 minutes utilizing ultrasound agitation. After this oxide removal step has been completed, the medical devices or parts are removed from the etching solution and rinsed with deionized water three successive times without exposing the medical devices or parts to air or oxygen to thereby prevent the formation of a new oxide on the surfaces of the parts. Although the etching solution selected may be varied, the particular etching solution identified above has been found to be efficacious to remove the oxide without creating pits in the metal.

After the parts have been washed with deionized water, the parts are introduced into a blanket of an inert atmosphere such as nitrogen gas in a hooded bench and are transferred into a saturated cystine solution. One solution found to be satisfactory is one comprising of 50% acetic acid and water with some undissolved cystine. The parts are left in the solution for a period of 8 to 12 hours at room temperature for shorter periods of time as for example ½ hour to 2 hours at elevated temperatures as for example at 60° C. The cystine solution which is an organic coupling agent or linker is placed in contact with the surface of the parts or in the case of the dental post in contact with the microspheres 17 carried by the cylindrical surface 16 to form an oxidative coupling with the surface as for example the surface of the metal microspheres. The oxidative reaction forms a very thin layer as for example a monolayer having a thickness of approximately 20A. In FIG. 2, this layer is represented as an exaggerated layer 26 which covers the microspheres 17. The oxidative coupling which occurs using the organic linker cystine occurs because the cystine has a disulfide bond and the sulfur acts as an oxidizing agent. At the same time it oxidizes, it binds itself to the metal which in the case of titanium creates a titanium-sulfur covalent bond.

It should be appreciated that other organic linkers can be utilized in connection with the present invention for oxidizing metals and also for oxidizing polymers as hereinafter described. These oxidizers include organic peroxides, organic sulfoxide, sulfones and sulfonic acids. By placing the oxide-free surface of the medical device or part in contact with the organic linker, there is formed an oxidative coupling as shown by step 28 in FIG. 5.

After the oxidative coupling has been formed, the parts can be removed from the cystine solution and rinsed with deionized water. There is no longer need to keep the parts out of contact with air or oxygen because the oxidative reaction has already occurred during the formation of the oxidative coupling 28 represented by the layer 26 in FIG. 2.

Next a bioactive agent or growth promoter is attached as shown by step 31 in FIG. 5. This is accomplished by utilizing an organic coupling agent. For example, one commonly available is EDC which is 1-(3-Dimethylaminopropyl)-3-ethylcarbodiimide HCl. The purpose of this coupling agent is to cause the bioactive agent to become attached to the surface of the foreign body by a reaction with the organic linker. The reaction can be any one of a number of types as for example a condensation reaction, oxidative reaction, an exchange reaction and a substitution reaction. In other words, the bond is one which is formed by a reactive function. Thus a variety of organic reactions can be used, resulting for example in an ester, ether or a carbon-carbon bond. When an unsaturated double bond is present, a polymerization reaction may be used.

In step 31 in which the bioactive agent is attached, it is desirable to place in this solution a small amount of a peptide which is a polymeric material but of a smaller chain length than proteins. For example, a 15-amino acid along cell binding peptide can be utilized of the type disclosed in U.S. Pat. No. 5,354,736. In step 31 shown in FIG. 5, it is desirable that the reactive function and the peptide react together to form an amide bond. Thus, there can be provided an amino terminal bound bioactive agent or a carboxyl terminal bound bioactive agent.

It should be appreciated that if desired, materials other than growth promoters can be adhered to surface in the manner hereinbefore described. For example Heparin, although not a growth promoter, can be adhered to the metal in a similar method. This attachment of a bioactive agent implemented by step 31 is represented by the layer 32 as shown in FIG. 2.

Step 31 can be carried out at room temperature at a period of time ranging from 4 to 8 hours and preferably about 6 hours. In an elevated temperature as for example, 60° C., the same reaction can be accomplished in approximately 2 to 3 hours.

Figure 3:
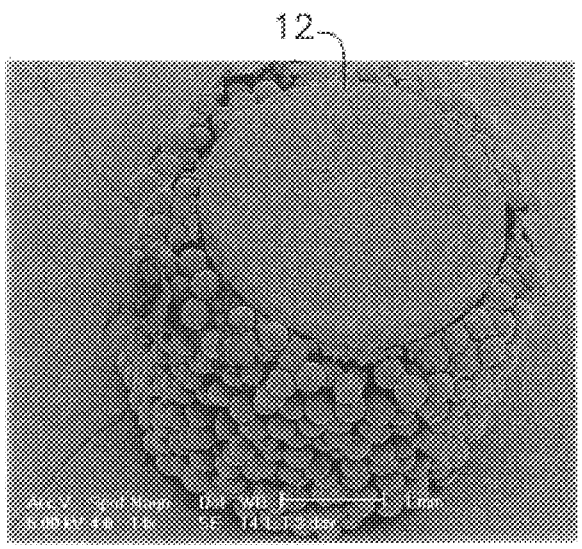
FIG. 3 is a photograph taken with an electron microscope showing the growth of cells on the base of the dental post after the base of the dental post has been treated in the method of the present invention.
Figure 4:
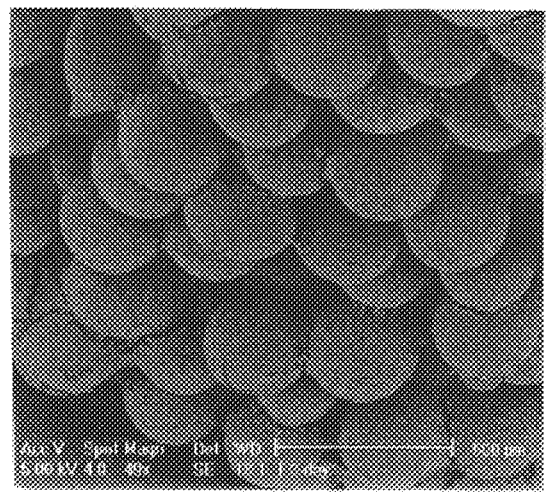
FIG. 4 is another photograph taken with an electron microscope of the outer surface of the base shown in FIG. 3 showing the manner in which human osteoblast cells have proliferated on the globular surfaces of the globules carried by the base of the dental post.

In FIGS. 3 and 4 there are shown photographs taken with an electron microscope of the medical device in the form of the dental post 11 which has been treated in accordance with the present invention. In FIG. 3 there has been a spot magnification of 14 times and in FIG. 4 a spot magnification of 49 times. The dental post after being subjected to the method hereinbefore described was placed in a tissue culture having therein grown human osteoblast cells. The growth promoter used had a peptide identified as P15 produced in accordance with the teaching of U.S. Pat. No. 5,354,736. In a period of three days it was found that with the biocompatible coating applied in accordance with the present invention, the cells from the tissue culture grew onto the surfaces of the microspheres 17 substantially as if they were in normal surroundings. Thus the cells did proliferate all over the coated surface indicating the efficacy of the biocompatible coating of the present invention. This was compared to a similar uncoated medical device placed in similar tissue culture in which very few cells from the human osteoblast cells adhered to the surface and none adhered where they were not in actual contact with the cells.

Figure 6:
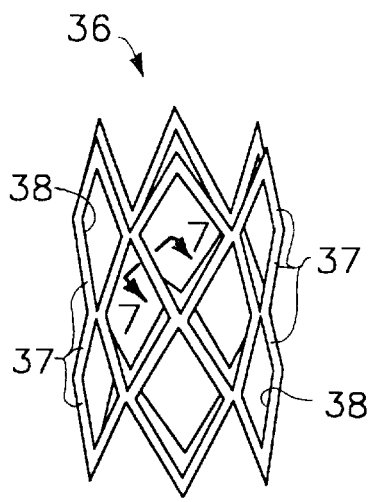
FIG. 6 is an isometric view of an expandable stent which has a biocompatible coating thereon applied in accordance with the present invention.
Figure 7:
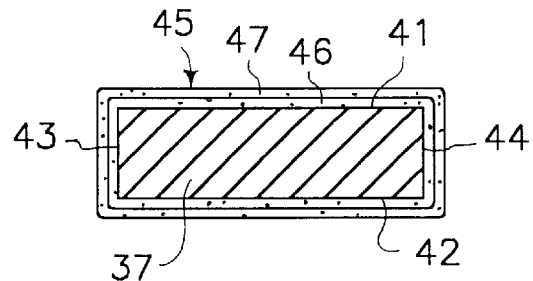
FIG. 7 is a cross-sectional view taken along the line 7—7 of FIG. 6.

Another medical device having a biocompatible coating thereon incorporating the present invention is shown in FIG. 6 in the form of an expandable deformable stent 36 in which the stent is formed by elongated elements 37 formed of a suitable biocompatible material such as titanium, nickel titanium alloys and like as hereinbefore described which have diamond shaped openings 38 between the same through which tissue can grow. It has been found desirable to coat these elements 37 with a biocompatible coating in accordance with the present invention. As shown in FIG. 7, a cross-sectional view of one of the elements 37 has an outer surface 41, an inner surface 42 and end surfaces 43 and 44, all of which are coated with a biocompatible coating 45 of the present invention. Thus there has been provided an organic linker represented by a layer 46 which forms an oxidative coupling with the surfaces 41, 42, 43 and 44. A bioactive agent is bonded to the organic linker by a reaction function in the manner hereinbefore described and is represented by the layer 47. Thus it can be seen in connection with the present invention that all of the exposed surfaces of the stent 36 are covered with the biocompatible coating of the present invention to greatly promote the growth of endothelial cells on the same after the stent has been implanted in a vessel of the human body to maintain the patency of a vessel in the patient, as for example in an angioplasty procedure.

Figure 8:
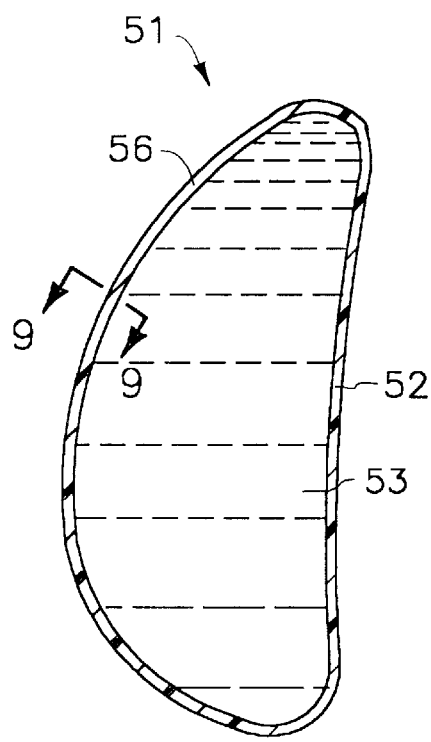
FIG. 8 is a cross-sectional view of a breast implant in which a biocompatible coating has been applied in accordance with the present invention.
Figure 9:
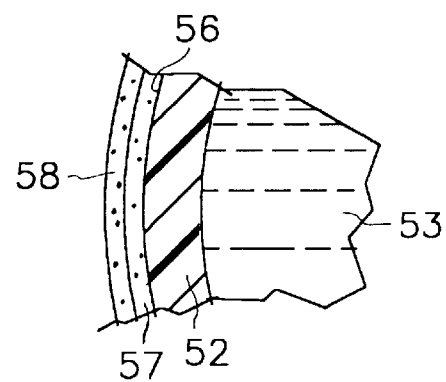
FIG. 9 is a cross-sectional view taken along the line 9—9 of FIG. 8.

Another embodiment of the invention is shown in FIG. 8 in which the medical device 51 is in the form of a breast implant. Typically such breast implants have a flexible plastic envelope 52 formed of a suitable material such as a polyurethane or a polyester. The interior of the envelope is filled with a suitable liquid 53 such as silicon or a variety of vegetable oils such as soy bean oil. The envelope 52 has an exterior surface 56 which is adapted to be placed in engagement with the tissue of the human body. This exterior surface 56 is treated in the same manner as the exterior surfaces of the metal medical devices hereinbefore described.

The breast implant is dipped in a suitable oxidizing agent such as an organic peroxide for a suitable period of time ranging from a few minutes to an hour depending upon the nature of the plastic and the reagent utilized. Thereafter, the breast implant can be removed from the oxidizing agent and washed with deionized water after which it is placed in a solution of the desired growth promoter along with other reagents to enhance the rate of reaction. Thus, the coupling agent and the growth promoter are placed in the same solution so that they can coact in the solution over a suitable period of time as for example 5 to 6 hours at room temperature. At elevated temperatures the reaction takes place within a few minutes to within an hour. Thereafter, the breast implant can be removed from the solution, washed in deionized water, dried and packaged for shipment for later use.

In connection with the present invention, it can be seen that there has been provided a biocompatible coating on medical devices including plastic and metal devices which although foreign objects in the human body are disguised from the human autoimmune system and leading the autoimmune system of the human body to believe that the device is not a foreign body and thus will encourage cell growth on the same by providing a foundation for such cell growth. The medical devices on which the present invention would be useful include the following: cardiovascular devices, including implantable defibrillators, implantable defibrillator leads, pacemakers and pacemaker leads, artificial heart valves, LVAD's, stents, stent grafts, soft tissue implant devices including implantable pumps, implantable leads, cochlear implants, implants for reconstructive surgery, urinary incontinence devices, penile and breast implants, and surgical aids including sutures, vascular occlusion devices and surgical supplies.

I claim:

1. A medical device for implantation in the tissue of a human body having a biocompatible coating thereon, said device comprising a foreign body formed of a material which is substantially biocompatible with the tissue of the human body, said foreign body having a surface adapted to come in contact with the tissue of the human body, said surface being capable of being oxidized, said coating including an organic linker bonded directly to said surface and forming an oxidative coupling with said surface, and a bioactive agent bonded to the organic linker by a reactive function.

2. A device as in claim 1 wherein said organic linker is selected from the group consisting of cystines, organic peroxides, organic sulfone, sulfoxide and sulfonic acids.

3. A device as in claim 2 wherein said bioactive agent is selected from the group consisting of growth promoters, anti-thrombogenic agents, steroids, antibiotics, hormones and cytokines.

4. A device as in claim 3 wherein said bioactive agent includes a peptide.

5. A device as in claim 4 wherein said peptide is in a form of 15 amino acid long cell binding peptide.

6. A device as in claim 1 wherein said reactive function is capable of undergoing a reaction selected from the group consisting of a condensation reaction, oxidative reaction, exchange reaction and substitution reaction.

7. A device as in claim 1 wherein said device is formed of a metal which is substantially biocompatible with the human body.

8. A device as in claim 7 wherein said metal is selected from the group consisting of stainless steel, titanium, and alloys of titanium.

9. A device as in claim 1 wherein said device is a dental post.

10. A device as in claim 1 wherein said device is a stent.

11. A device as in claim 1 wherein said material is formed of plastic.

12. A device as in claim 1 wherein said device is a breast implant.

* * * * *